United States Patent
Jagdale

(10) Patent No.: US 12,302,869 B2
(45) Date of Patent: May 20, 2025

(54) SYSTEM AND DEVICES FOR MANAGING A POULTRY FARM

(71) Applicant: PAKSHIMITRA POULTRY TECHNOLOGIES PRIVATE LIMITED, Maharashtra (IN)

(72) Inventor: Shankar Babaji Jagdale, Pune (IN)

(73) Assignee: PAKSHIMITRA POULTRY TECHNOLOGIES PRIVATE LIMITED, Pune (IN)

( * ) Notice: Subject to any disclaimer, the term of this patent is extended or adjusted under 35 U.S.C. 154(b) by 0 days.

(21) Appl. No.: 18/034,862

(22) PCT Filed: Jun. 2, 2022

(86) PCT No.: PCT/IN2022/050514
§ 371 (c)(1),
(2) Date: May 1, 2023

(87) PCT Pub. No.: WO2023/195016
PCT Pub. Date: Oct. 12, 2023

(65) Prior Publication Data
US 2024/0341288 A1    Oct. 17, 2024

(30) Foreign Application Priority Data
Apr. 7, 2022   (IN) .............................. 202221021027

(51) Int. Cl.
*A01K 45/00* (2006.01)
*A01K 1/00* (2006.01)
(Continued)

(52) U.S. Cl.
CPC ............ *A01K 45/00* (2013.01); *A01K 1/0047* (2013.01); *A01K 1/0082* (2013.01);
(Continued)

(58) Field of Classification Search
CPC .... A01K 45/00; A01K 1/0047; A01K 1/0082; A01K 1/0135; A01K 31/165; A01K 39/04; A61L 2/10; A61L 2/22
(Continued)

(56) References Cited

U.S. PATENT DOCUMENTS 5,143,309 A * 9/1992 Endom ................ A01B 33/021
                                                     241/189.1
5,901,911 A * 5/1999 Davis .................. A01K 1/0146
                                                     241/101.77
(Continued)

FOREIGN PATENT DOCUMENTS

BR    202017023462 U2    6/2019
CN         108999253 A   12/2018
(Continued)

OTHER PUBLICATIONS

Indian Examination Report dated May 30, 2022 as received in application No. 202221021027.
(Continued)

*Primary Examiner* — Hung Q Nguyen
*Assistant Examiner* — Anthony Donald Taylor, Jr.
(74) *Attorney, Agent, or Firm* — Maschoff Brennan

(57) ABSTRACT

Disclosed is a system (100) for a poultry farm. The system (100) includes an automated guided vehicle (110). The automated guided vehicle (110) includes a body (111) adapted to mount a plurality of devices (170), a plurality of wheels (112), a plurality of sensors (113), a collection bin (114) at the rear end (116) of the automated guided vehicle (110), and a detachable protection arrangement (160) at a front (115) of the body (111). The system (100) also includes an overhead power railing unit (120), an open overhead utility line (130) with a vertical water supply line (140) with a pump (142), and a vertical conveyor (150) to retrieve the
(Continued)

litter, eggs or wastewater from the collection bin (114) and dispose in the open overhead utility line (130).

14 Claims, 13 Drawing Sheets

(51) Int. Cl.
    *A01K 1/01*     (2006.01)
    *A01K 31/16*     (2006.01)
    *A01K 39/04*     (2006.01)
    *A61L 2/10*     (2006.01)
    *A61L 2/22*     (2006.01)

(52) U.S. Cl.
    CPC .......... *A01K 1/0135* (2013.01); *A01K 31/165* (2013.01); *A01K 39/04* (2013.01); *A61L 2/10* (2013.01); *A61L 2/22* (2013.01)

(58) Field of Classification Search
    USPC .......................................................... 701/41
    See application file for complete search history.

(56) References Cited

U.S. PATENT DOCUMENTS

| | | | |
|---|---|---|---|
| 2007/0051757 A1* | 3/2007 | Lim .................... | A47L 9/2852 |
| | | | 222/630 |
| 2014/0230737 A1* | 8/2014 | Hendricus ............ | A01K 5/0266 |
| | | | 119/57.92 |
| 2019/0166788 A1* | 6/2019 | Xu ........................ | A01K 1/0146 |
| 2019/0307106 A1* | 10/2019 | Hartung ................ | A01K 29/00 |
| 2019/0335651 A1* | 11/2019 | Altomare ............ | B01F 33/5021 |
| 2020/0178505 A1* | 6/2020 | Womble ............... | A01K 5/0291 |
| 2021/0076634 A1* | 3/2021 | Xu ........................ | A01K 29/005 |

FOREIGN PATENT DOCUMENTS

| CN | 114080996 A | 2/2022 |
|---|---|---|
| KR | 101695557 B1 | 1/2017 |

OTHER PUBLICATIONS

Ren et al., "Agricultural robotics research applicable to poultry production: A review" Computers and Electronics in Agriculture 169 (2020) 105216.

* cited by examiner

SYSTEM AND DEVICES FOR MANAGING A POULTRY FARM

FIELD OF THE INVENTION

The present disclosure relates to livestock farming machines and more particularly relates to systems and devices for managing a poultry farm.

BACKGROUND

Poultry such as broilers, livestock and the like meet the global demand for meat, eggs, and may more. To maintain productivity, the livestock should be free from pain, injury, or disease prevention of illnesses, or rapid diagnosis and treatment are a necessity. The livestock should be allowed to express normal behavior enough space, proper facilities and proper sanitation should be provided. Conditions and cleanliness should be provided which avoids illness and suffering.

However, the method of farming can lower the quality of life for the birds and can reduce the quality of the meat. Poultry should be kept from hunger and thirst live stocks must have access to fresh water and a diet which will maintain health and vigor. Poultry should be free from discomfort and an appropriate environment should be provided, including shelter and a comfortable resting area.

Generally, in poultry sheds, the air can become highly polluted with ammonia from the droppings. In this case, ventilation must be increased to bring in more clean fresh air. Furthermore, high ammonia levels can damage the broilers' or chickens' eyes and respiratory systems and can cause painful burns on their legs called hock burns and blisters on their feet. Ammonia is generated from wet bird's faeces containing uric acid by enzymatic and bacterial activity. If the litter can absorb the humidity bacterial activity is low and consequently, ammonia concentrations are low. Hence ammonia concentration in poultry house air depends largely on wet litter, animal density, and ventilation rate.

Therefore, broilers bred for fast growth have a high rate of leg deformities because large breast muscles cause distortions in developing legs and pelvis, and the birds cannot support their increased body weight. In cases where the broilers or chickens become crippled and can't walk. In such a scenario, human intervention is needed and farm personnel must go inside and pull out the effective birds and possibly kill them. Most losses tend to be in the first three to seven days or later at the end just before slaughter.

To overcome the abovementioned problems, technological developments have been done and devices have been developed to avoid human intervention and increase the productivity of the live stocks. Robots and automated machines have been developed that sweep the litter and collect the eggs and deadstock from the poultry farm. However, the conventional systems are difficult in using between the live stocks due to complex and huge designs that scare the live stocks and hampers the productivity of the live stocks.

Therefore, in light of foregoing discussions, there is a need to overcome the limitations/drawbacks of the conventional systems that operate inside the poultry farm between the live stocks.

SUMMARY

This summary is provided to introduce a selection of concepts, in a simplified format, that are further described in the detailed description of the invention. This summary is neither intended to identify key or essential inventive concepts of the invention and nor is it intended for determining the scope of the invention.

The present disclosure relates to a system for a poultry farm, such as a broiler poultry farm. The poultry farm as stated herein relates to chicken farms, broiler farms, breeder farm, layer farms, and the like. The present disclosure provides an efficient and automated system to manage live stocks in the poultry farm by processing and/or collecting the litter and thereby maintaining good health of the live stocks therein. In an example, the live stocks may include chicken, pigs, cattle, and the like.

In an aspect, according to the embodiments of the present disclosure, the system includes an automated guided vehicle adapted to traverse inside the poultry farm. The automated guided vehicle includes a body adapted to mount a plurality of devices to perform operations inside the poultry farm between live stocks, a plurality of wheels coupled to the body and adapted to move the automated guided vehicle inside the poultry farm, a plurality of sensors to capture environmental parameters at floor level inside the poultry farm, a collection bin at the rear end of the automated guided vehicle to receive at least one of the litter, eggs, and wastewater, and a detachable protection plate at a front of the body.

The system also includes an overhead power railing slidably coupled to the body of the automated guided vehicle via an overhead connector to transmit the power through stripes and sliding contact head, an open overhead utility line with a conveyor arrangement to receive and convey litter, egg, and water inside the poultry farm or the animal husbandry farm and the like, a vertical water supply line with pump at a top end is configured to supply fresh water from the open overhead utility line operatively coupled to the automated guided vehicle, and a vertical conveyor arrangement to retrieve the litter, eggs or wastewater from the collection bin and dispose in the open overhead utility line.

In another aspect, the plurality of devices includes a litter processing device for processing litter inside the poultry farm, a litter collector device for collecting litter inside the poultry farm and the like, a line cleaner device for cleaning the drinkers and feeders inside the poultry farm, an egg collection device for collecting eggs from the floor inside the poultry farm, a handling device for removal of dead or unhealthy livestock from the poultry farm, and a humidity control device for humidifying or dehumidifying air inside the poultry farm.

In yet another aspect, the overhead power railing system includes a holder coupled to railing housing arranged to a roof of the poultry farm, a sliding contact head is coupled to railing housing and configured with power stripes, adopted to slide therein, a wheel track coupled to railing housing, and a pair of motor driven wheels coupled to sliding contact head and configured to move on the wheel track in synchronization with a guided vehicle. The stripes of overhead power railing are connected to an AC or DC power source from one end of the poultry farm.

In one aspect, the handling device includes a robotic arm with a gripper arranged at the front end along with an image processing-based control unit to identify, lifting, and dropping of dead or unhealthy livestock in a collection bucket at the rear end.

In a second aspect, the humidity control device includes a humidifying unit to increase humidity of air inside the poultry farm using fresh water, and a dehumidifying unit to lower the humidity of air inside the poultry farm by collecting and disposing the water using a vertical conveyor and an overhead utility line.

In a third aspect, the present disclosure relates to a litter collector device for collecting litter in the poultry farm and the like. The litter collector device includes a rotary sweeper mounted proximate to a collector shovel arranged at the front end with level adjustment arrangement and adapted to lift and gather litter. The litter collector device also includes a belt conveyor positioned adjacent to the collector shovel and operable to transfer the litter from the collector shovel to a litter collector mounted at a rear end of the belt conveyor.

In a fourth aspect, the present disclosure relates to a litter processing device for processing a litter inside a poultry farm. The litter processing device includes a tiller head positioned at a front end and operatively coupled to power drive, the tiller head adapted to crush litter scattered on a floor of the poultry farm, a heater unit positioned at a rear side of the tiller head and adapted to heat the crushed litter, a disinfector unit positioned at a rear side of the heater unit and configured to disinfect the crushed litter, and a disinfector storage tank mounted on the disinfector and adapted to pour disinfector on the crushed litter.

In a fifth aspect, the present disclosure relates to a line cleaner device for cleaning of feeder and drinker lines inside the poultry farm. The line cleaner device includes an enclosed chamber with collapsible doors at front and rear end to allow passage for a feeder or a drinking water pan adapted to avoid splashing of water outside the chamber, a water sprayer with a plurality of spray nozzles for spraying water to clean the feeder or drinking water pan, a pair of a cleaner and a dryer to wipe out the water and dry out feeder and drinking water pan, a collecting pan at the bottom to collect the wastewater after cleaning operation with a slope towards an outlet nozzle connected to a collection chamber.

In a sixth aspect, the present disclosure relates to an egg collection device for collecting floor eggs from a poultry farm. The egg collection device includes a rotary sweeper and shovel arranged at a front end of the egg collection device and adapted to inwardly sweep eggs at a predefined speed, an egg collector plate proximate to the rotary sweeper and adapted to allow lifting of eggs swept from the rotary sweeper, a pair of rotatable bars mounted parallel to each other at a distance to accommodate at least one egg thereupon and adapted to separate litter from eggs, wherein the pair of rotatable bars are arranged at a rear end of the egg collector plate and configured to allow landing of eggs therein from the egg collector plate, and a horizontal conveyor with spikes to guide or push the eggs on the rotatable bars towards a collection tray.

To further clarify advantages and features of the present invention, a more particular description of the invention will be rendered by reference to specific embodiments thereof, which is illustrated in the appended drawings. It is appreciated that these drawings depict only typical embodiments of the invention and are therefore not to be considered limiting of its scope. The invention will be described and explained with additional specificity and detail with the accompanying drawings.

BRIEF DESCRIPTION OF THE DRAWINGS

These and other features, aspects, and advantages of the present invention will become better understood when the following detailed description is read with reference to the accompanying drawings in which like characters represent like parts throughout the drawings, wherein.

Figure 1A:
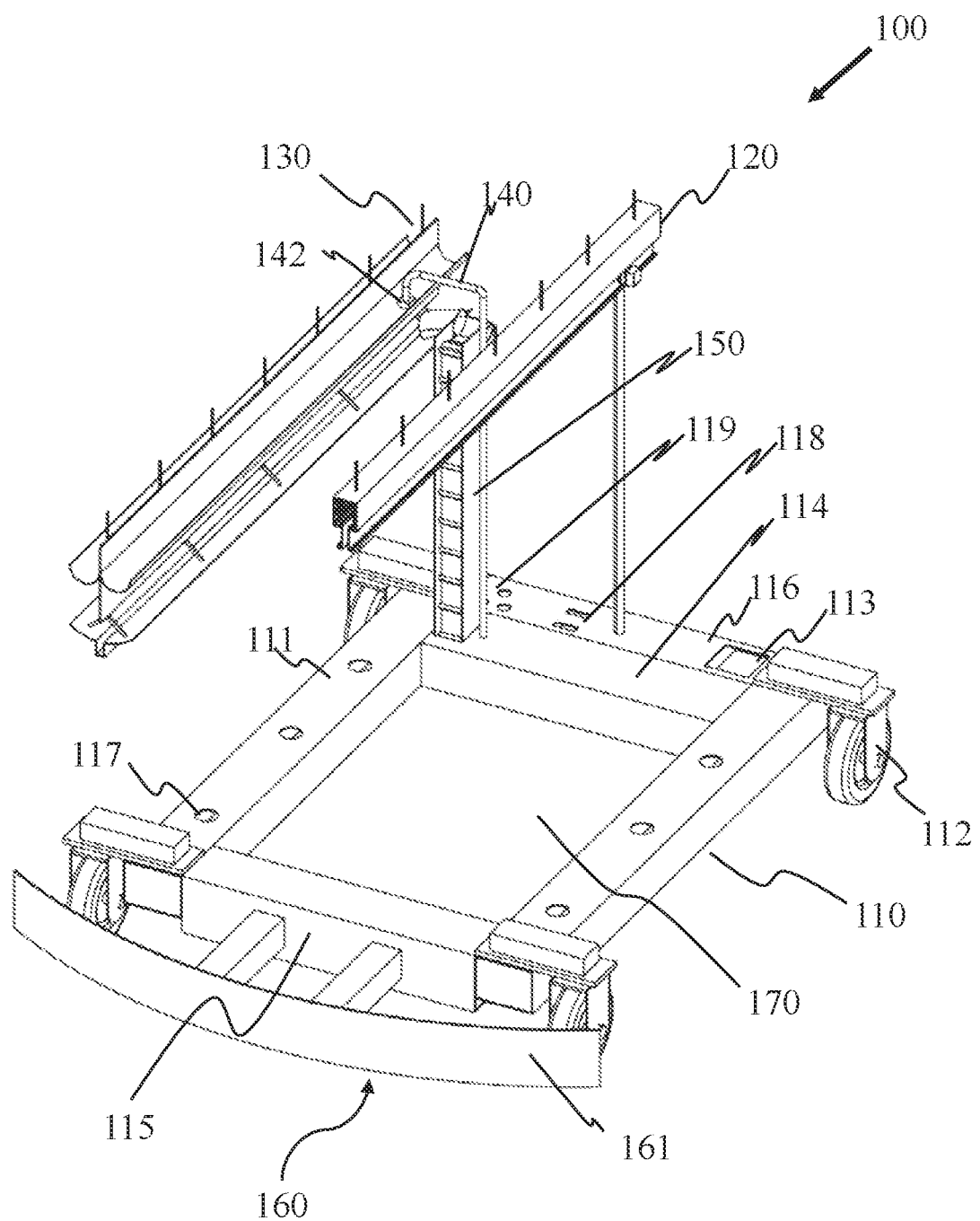
FIG. 1A illustrates a system for a poultry farm, according to an embodiment of the present disclosure.

Further, skilled artisans will appreciate that elements in the drawings are illustrated for simplicity and may not have necessarily been drawn to scale. Furthermore, in terms of the construction of the device, one or more components of the device may have been represented in the drawings by conventional symbols, and the drawings may show only those specific details that are pertinent to understanding the embodiments of the present invention so as not to obscure the drawings with details that will be readily apparent to those of ordinary skill in the art having benefit of the description herein.

DETAILED DESCRIPTION OF FIGURES

For the purpose of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated system, and such further applications of the principles of the invention as illustrated therein being contemplated as would normally occur to one skilled in the art to which the invention relates. Unless otherwise defined, all technical and scientific terms used herein have the same meaning as commonly understood by one of ordinary skilled in the art to which invention belongs. The system and examples provided herein are illustrative only and not intended to be limiting.

For example, the term "some" as used herein may be understood as "none" or "one" or "more than one" or "all." Therefore, the terms "none," "one," "more than one," "more than one, but not all" or "all" would fall under the definition of "some." It should be appreciated by a person skilled in the art that the terminology and structure employed herein is for describing, teaching, and illuminating some embodiments and their specific features and elements and therefore, should not be construed to limit, restrict or reduce the spirit and scope of the present disclosure in any way.

For example, any terms used herein such as, "includes," "comprises," "has," "consists," and similar grammatical variants do not specify an exact limitation or restriction, and certainly do not exclude the possible addition of one or more features or elements, unless otherwise stated. Further, such terms must not be taken to exclude the possible removal of one or more of the listed features and elements, unless otherwise stated, for example, by using the limiting language including, but not limited to, "must comprise" or "needs to include."

Whether or not a certain feature or element was limited to being used only once, it may still be referred to as "one or more features" or "one or more elements" or "at least one feature" or "at least one element." Furthermore, the use of the terms "one or more" or "at least one" feature or element do not preclude there being none of that feature or element, unless otherwise specified by limiting language including, but not limited to, "there needs to be one or more . . . " or "one or more elements is required."

Unless otherwise defined, all terms and especially any technical and/or scientific terms, used herein may be taken to have the same meaning as commonly understood by a person ordinarily skilled in the art.

Reference is made herein to some "embodiments." It should be understood that an embodiment is an example of a possible implementation of any features and/or elements of the present disclosure. Some embodiments have been described for the purpose of explaining one or more of the potential ways in which the specific features and/or elements of the proposed disclosure fulfil the requirements of uniqueness, utility, and non-obviousness.

Use of the phrases and/or terms including, but not limited to, "a first embodiment," "a further embodiment," "an alternate embodiment," "one embodiment," "an embodiment," "multiple embodiments," "some embodiments," "other embodiments," "further embodiment", "furthermore embodiment", "additional embodiment" or other variants thereof do not necessarily refer to the same embodiments. Unless otherwise specified, one or more particular features and/or elements described in connection with one or more embodiments may be found in one embodiment, or may be found in more than one embodiment, or may be found in all embodiments, or may be found in no embodiments. Although one or more features and/or elements may be described herein in the context of only a single embodiment, or in the context of more than one embodiment, or in the context of all embodiments, the features and/or elements may instead be provided separately or in any appropriate combination or not at all. Conversely, any features and/or elements described in the context of separate embodiments may alternatively be realized as existing together in the context of a single embodiment.

Any particular and all details set forth herein are used in the context of some embodiments and therefore should not necessarily be taken as limiting factors to the proposed disclosure.

Embodiments of the present invention will be described below in detail with reference to the accompanying drawings.

For the sake of clarity, the first digit of a reference numeral of each component of the present disclosure is indicative of the Figure number, in which the corresponding component is shown. For example, reference numerals starting with digit "1" are shown at least in FIG. 1. Similarly, reference numerals starting with digit "2" are shown at least in FIG. 2.

Embodiments of the present disclosure herein relate to a system for a poultry farm. The system provides an automated guided vehicle that traverses inside the poultry farm and is adapted to travel in between the live stocks. The automated guided vehicle is configured to mount a plurality of devices thereupon to perform various operations inside the poultry farm. Such operations include processing litter, collecting litter, supplying water, removing deadstock, and collecting eggs therefrom. Beneficially, the system provides a universal solution for necessary operations such as processing litter, collecting litter, supplying water, removing deadstock, and collecting eggs inside the poultry farm. The system facilitates open overhead utility line with a conveyor arrangement to receive and convey litter, collect egg, and supply water inside the poultry farm. Also, the overhead utility line with open water channel to supply the fresh water inside the poultry farm The present disclosure also provides a modular system that may include multiple automated guided vehicles that are configured with various devices and adapted to perform one or more operations synchronously. Moreover, the multiple automated guided vehicles enhance the productivity of the poultry farm thereby reducing the input cost.

FIG. 1A illustrates a system 100 for a poultry farm, according to an embodiment of the present disclosure. The system 100 includes the automated guided vehicle 110 adapted to support different devices for managing a livestock farm and performing operations in the livestock farm. In an embodiment, referring to FIG. 1A, the automated guided vehicle 110 includes a body 111 adapted to mount a plurality of devices 170, a plurality of wheels 112, a plurality of sensors 113, a collection bin 114 at a rear end 116 of the automated guided vehicle 110, and a detachable protection arrangement 160 at a front end 115 of the guided vehicle 110.

In an embodiment, the livestock farm may be embodied as a poultry farm. The system 100 and the plurality of devices 170 of the present disclosure are explained with respect to the poultry farm. However, it should be appreciated by a person skilled in the art that it should not be construed as limiting, and the system 100 and the plurality of devices 170 can be implemented for livestock farms having live stocks, such as cattle, pigs, etc.

Figure 1B:
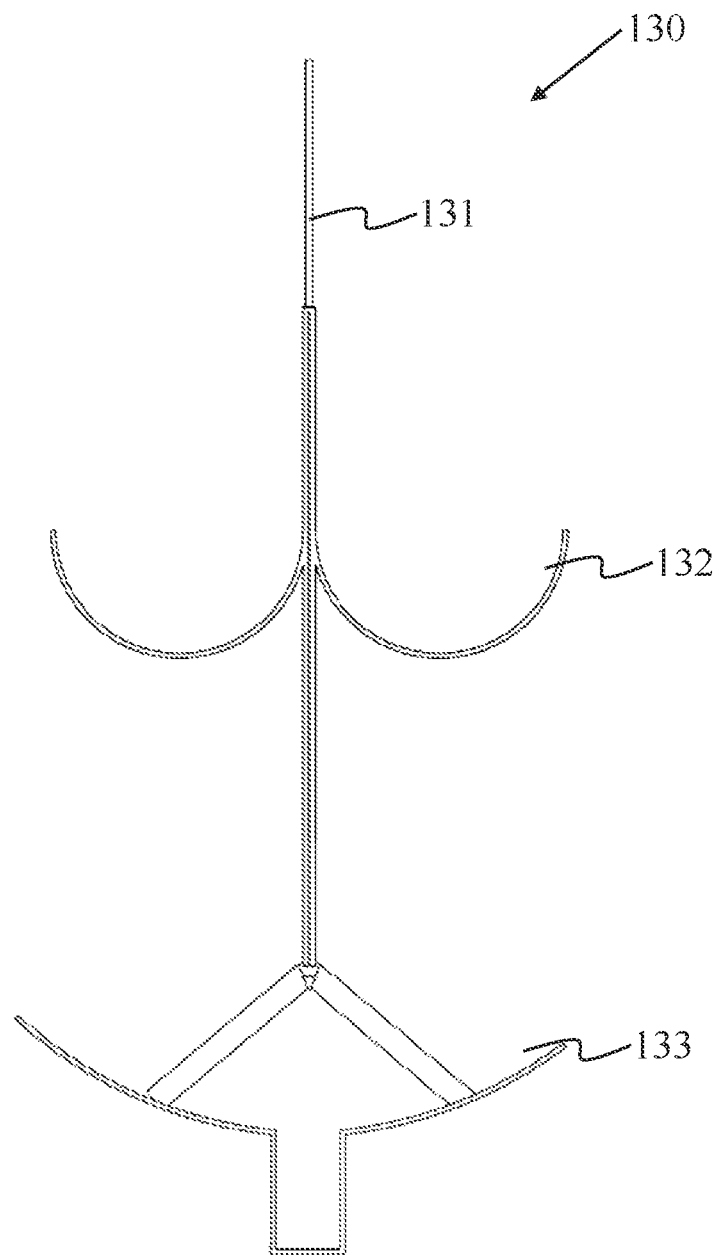
FIG. 1B illustrates a front view of an open overhead utility line, according to an embodiment of the present disclosure.
Figure 1C:
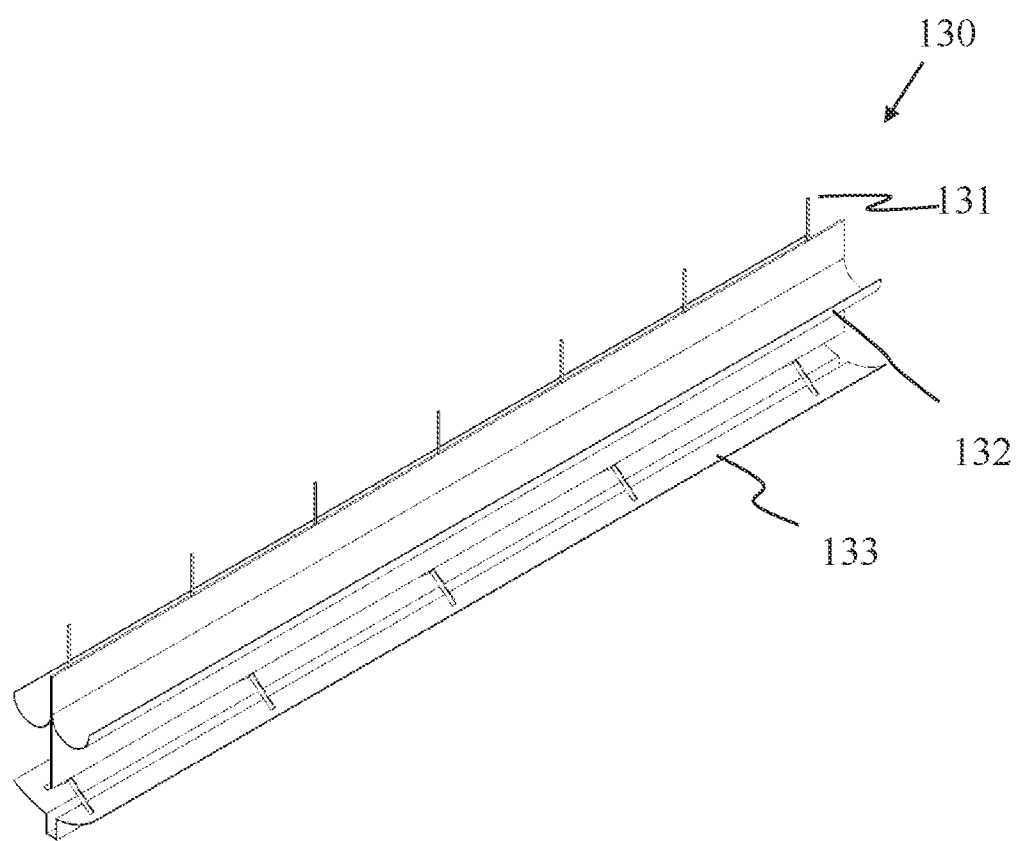
FIG. 1C illustrates a perspective view of the open overhead utility line, according to an embodiment of the present disclosure.
Figure 1D:
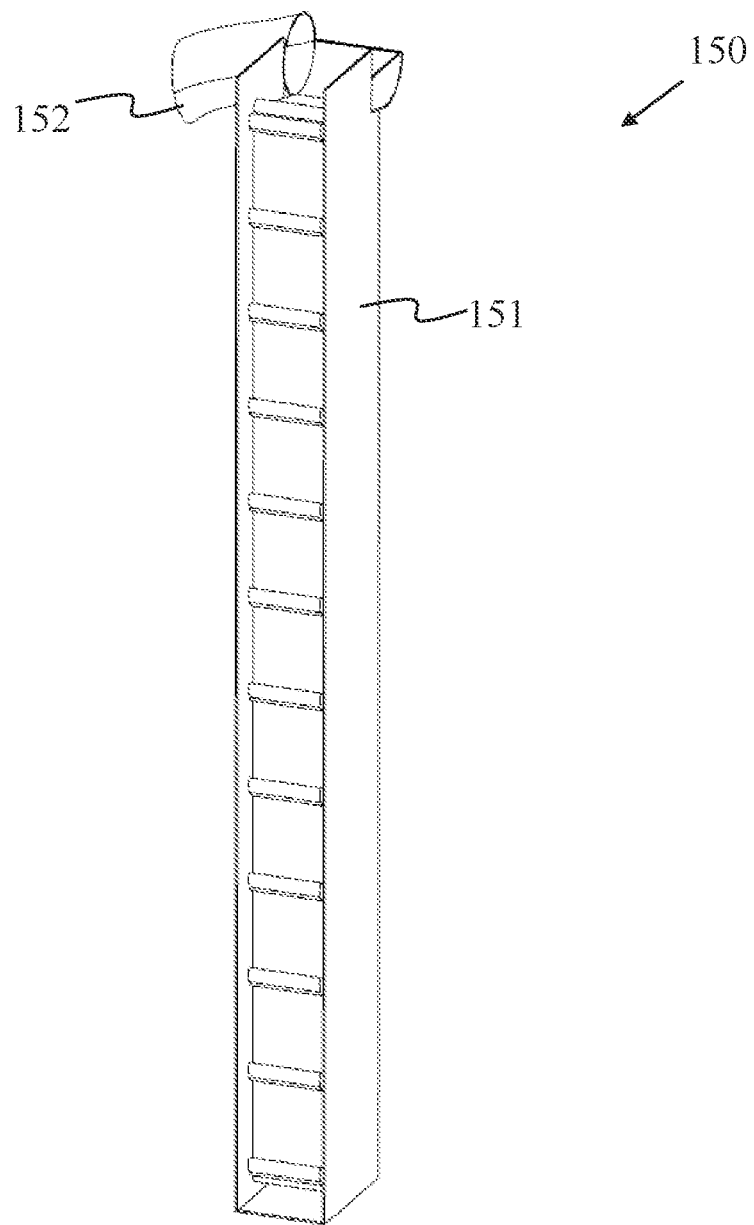
FIG. 1D illustrates a perspective view of a vertical conveyor arrangement, according to an embodiment of the present disclosure.
Figure 1E:
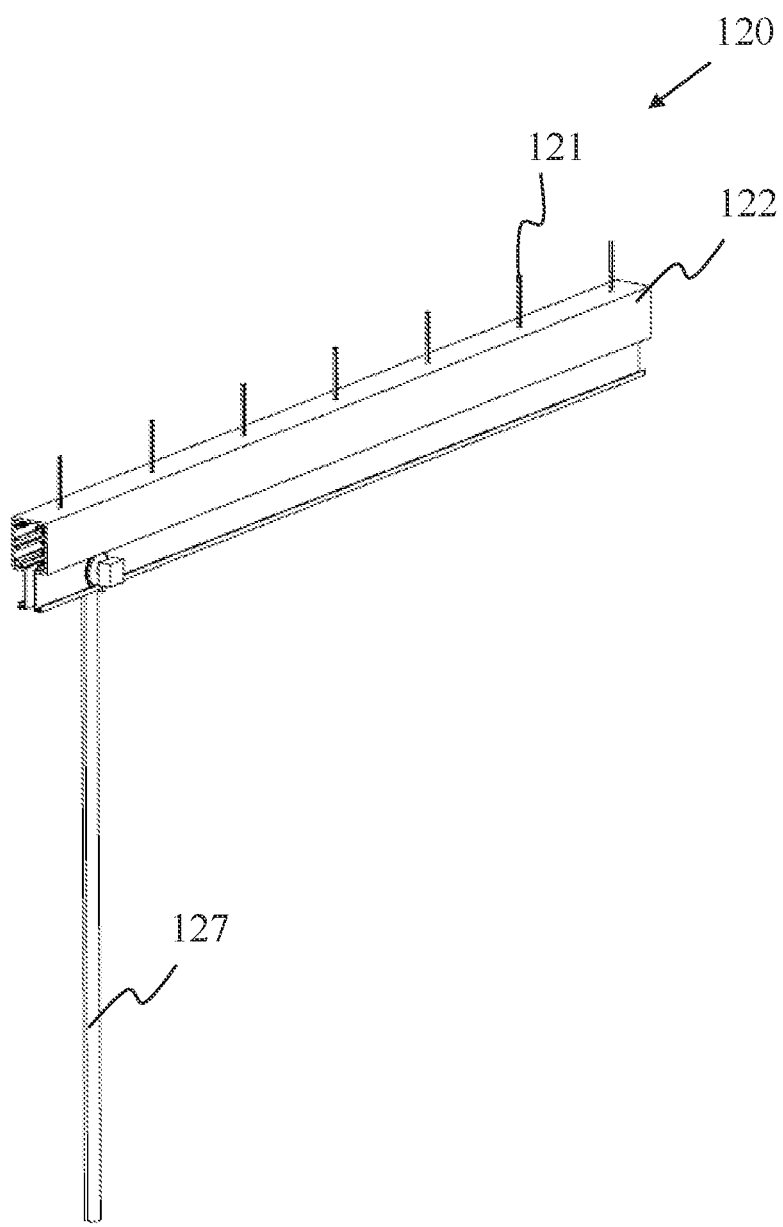
FIG. 1E illustrates the overhead power railing, according to an embodiment of the present disclosure.
Figure 1F:
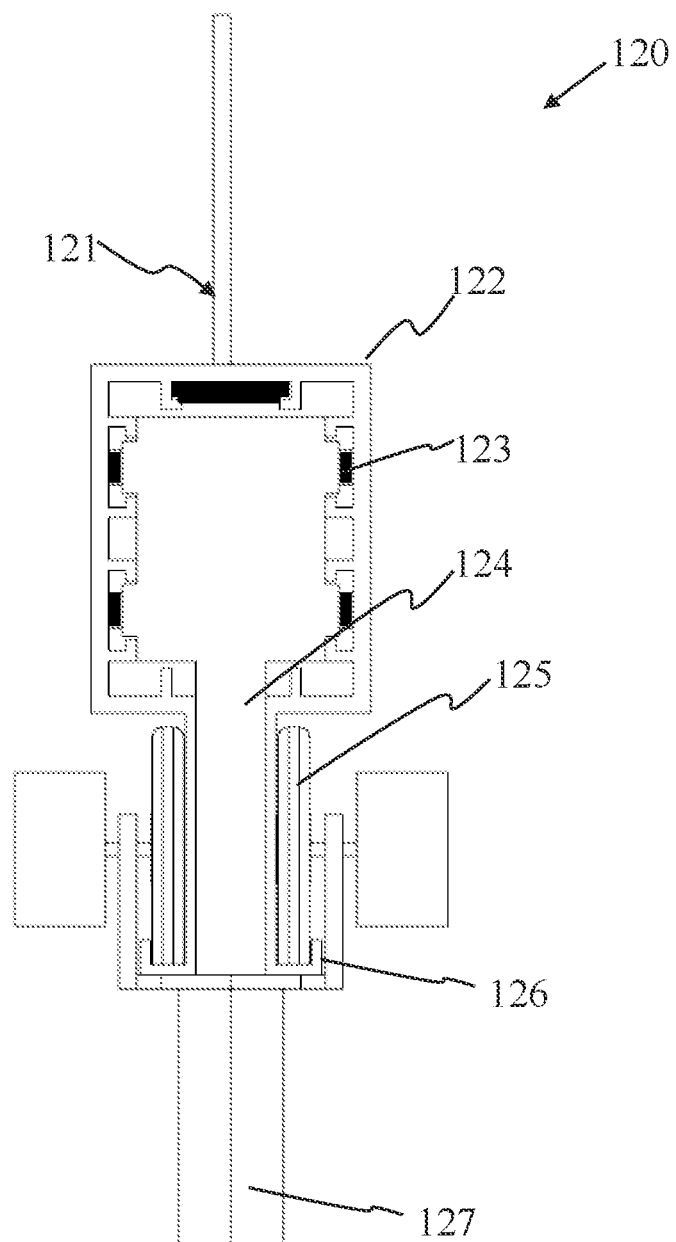
FIG. 1F illustrates a side view of an overhead power railing, according to an embodiment of the present disclosure.

FIG. 1B illustrates a front view of an open overhead utility line 130, according to an embodiment of the present disclosure. FIG. 1C illustrates a perspective view of the open overhead utility line 130, according to an embodiment of the present disclosure. FIG. 1D illustrates a perspective view of a vertical conveyor power 150, according to an embodiment of the present disclosure. FIG. 1E illustrates a perspective view of an overhead power railing 120, according to an embodiment of the present disclosure. FIG. 1F illustrates a side view of the overhead power railing 120, according to an embodiment of the present disclosure.

Referring to FIG. 1A, the automated guided vehicle 110 includes the body 111 adapted to mount a plurality of devices 170 to perform operations inside the poultry farm between live stocks. The term "automated guided vehicle" as used herein refers to an auto-bot or a robot or an autonomous vehicle that is communicably coupled to the overhead power railing 120, without departing from the scope of the present disclosure. The automated guided vehicle 110 is configured to move inside the poultry farm. In particular, the automated guided vehicle 110 is configured to move within an area of the poultry farm which accommodates the live stocks without scaring such live stocks. The automated guided vehicle 110 is in a compact design that is approximately in same height of the live stocks and therefore the compact design avoids scaring of the live stocks therein.

Furthermore, the automated guided vehicle 110 coupled with water supply that ensures continuous supply of water and power during the operation of the automated guided vehicle 110 and the plurality of devices 170. The automated guided vehicle 110 includes and is designed to work on a DC power input and an AC power input. In an embodiment, the automated guided vehicle 110 includes a DC power input port 118 and an AC power input port 119. Thus, the automated guided vehicle 110 is supplied the power to the plurality of devices 170, that runs by an AC power supply or DC power supply.

Figure 2:
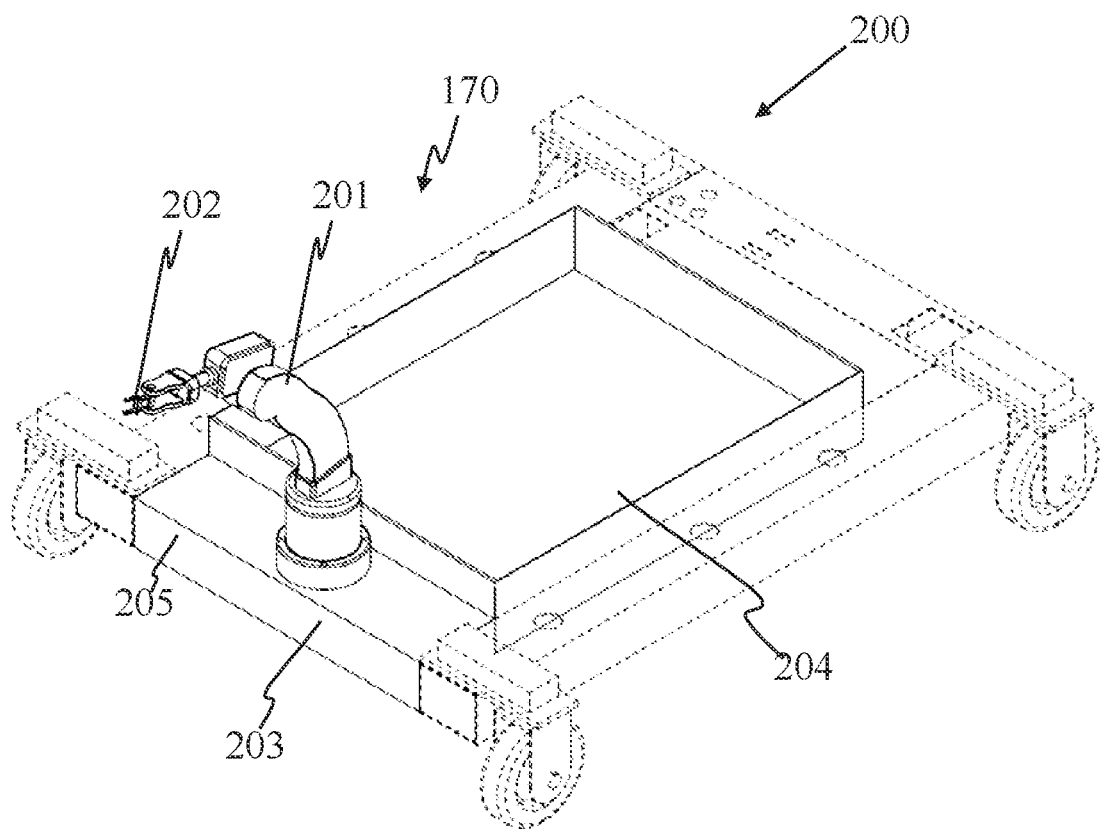
FIG. 2 illustrates the handling device for a poultry farm, according to an embodiment of the present disclosure.
Figure 3:
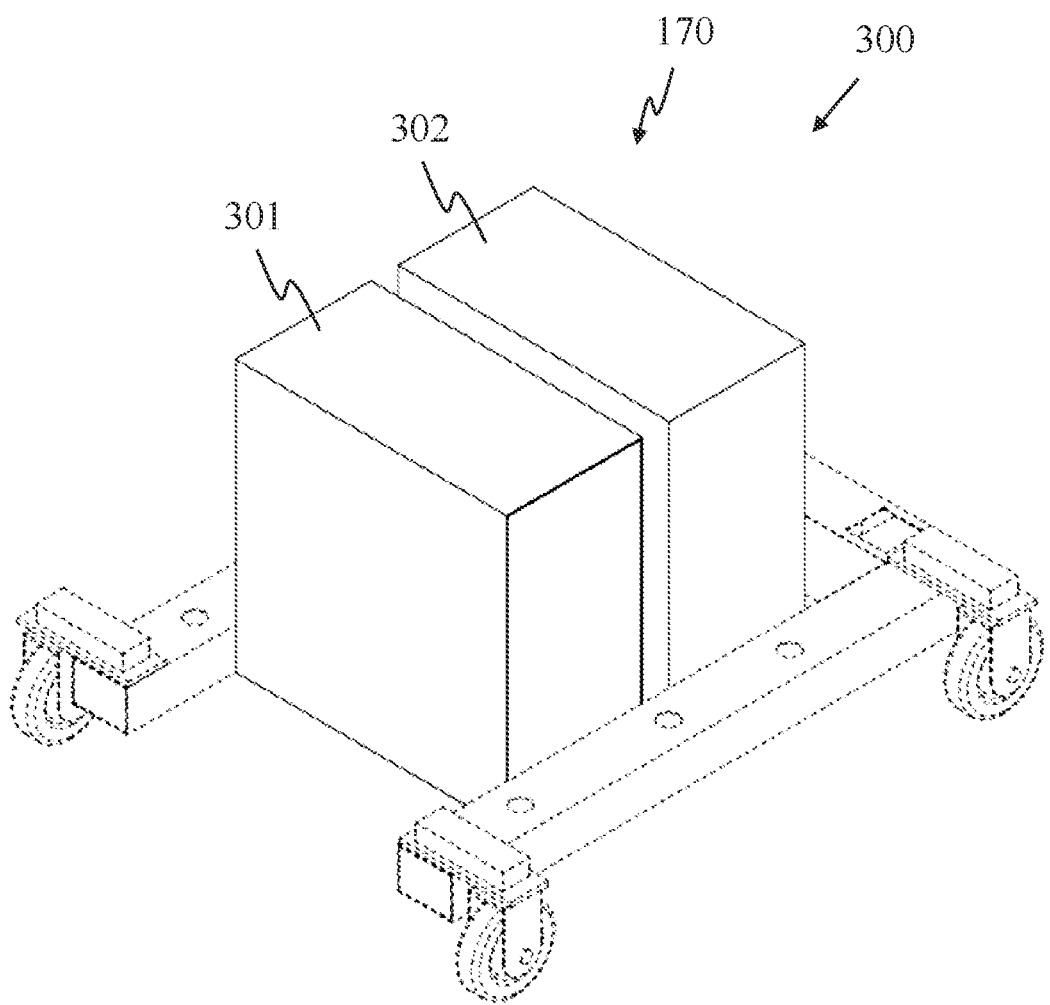
FIG. 3 illustrates the humidity control device for a poultry farm, according to an embodiment of the present disclosure.
Figure 4:
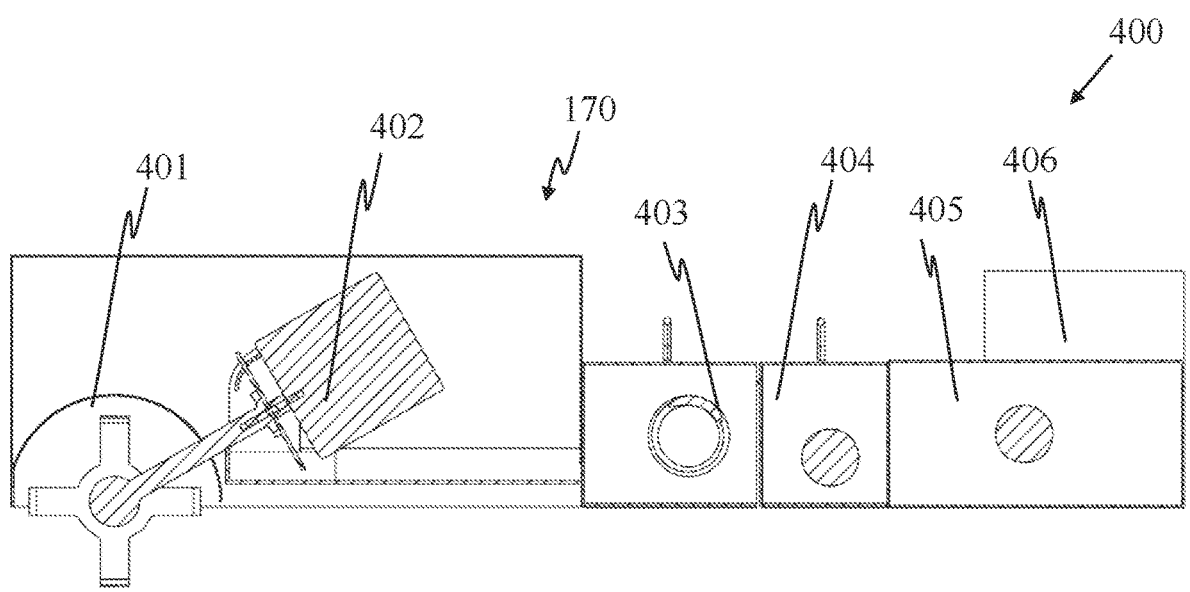
FIG. 4 illustrates the litter processing device for processing a litter inside a poultry farm, according to an embodiment of the present disclosure.
Figure 5:
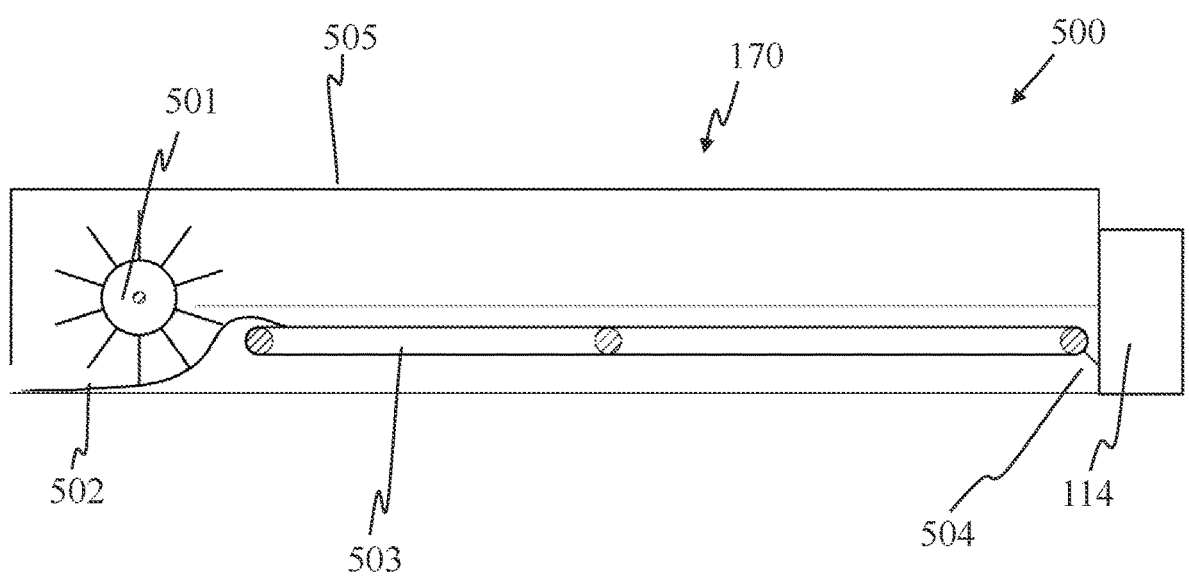
FIG. 5 illustrates a litter collection device for collecting litter in a poultry farm, according to an embodiment of the present disclosure.
Figure 6:
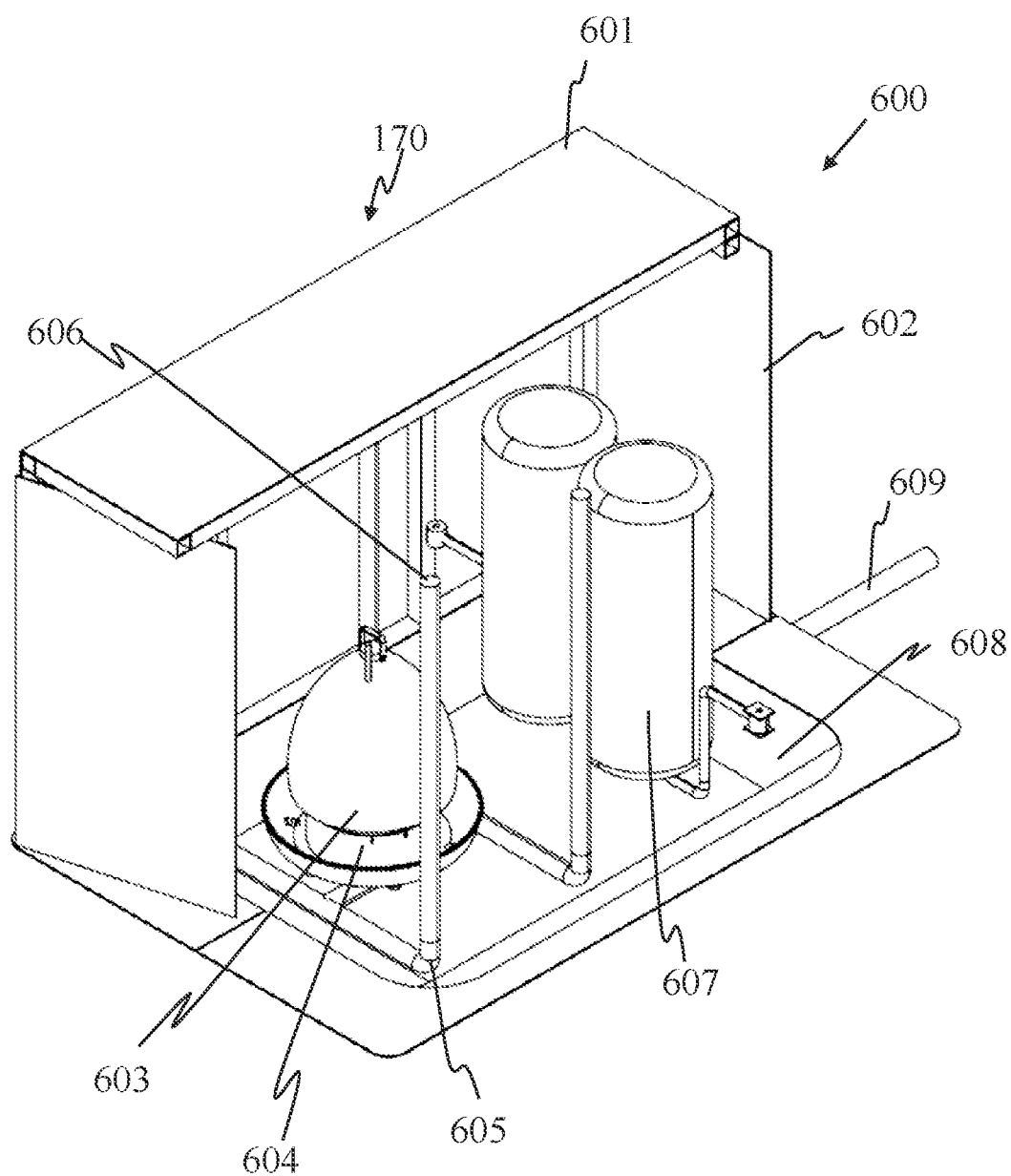
FIG. 6 illustrates a line cleaner device for cleaning of feeder and drinker lines inside the poultry farm, according to an embodiment of the present disclosure.
Figure 7A:
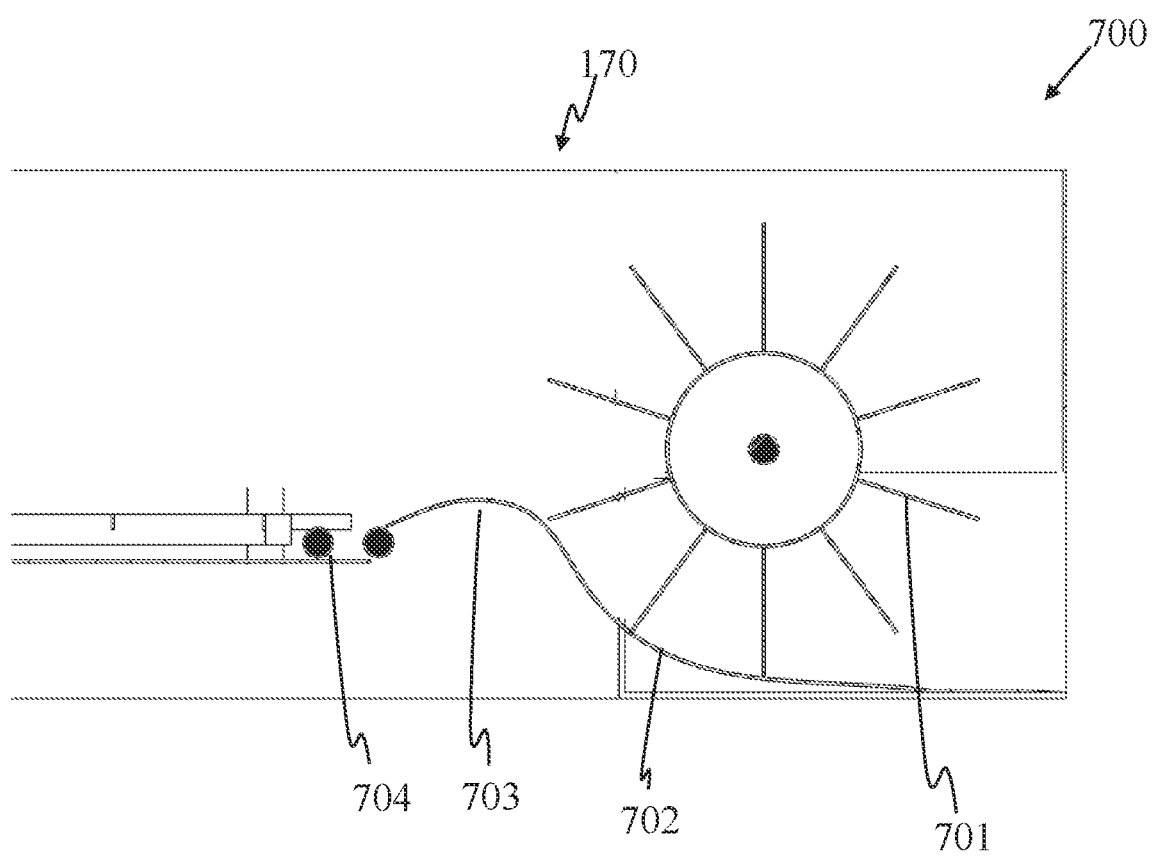
FIG. 7A illustrates a side view of an egg collection device for collecting floor eggs from a poultry farm, according to an embodiment of the present disclosure.
Figure 7B:
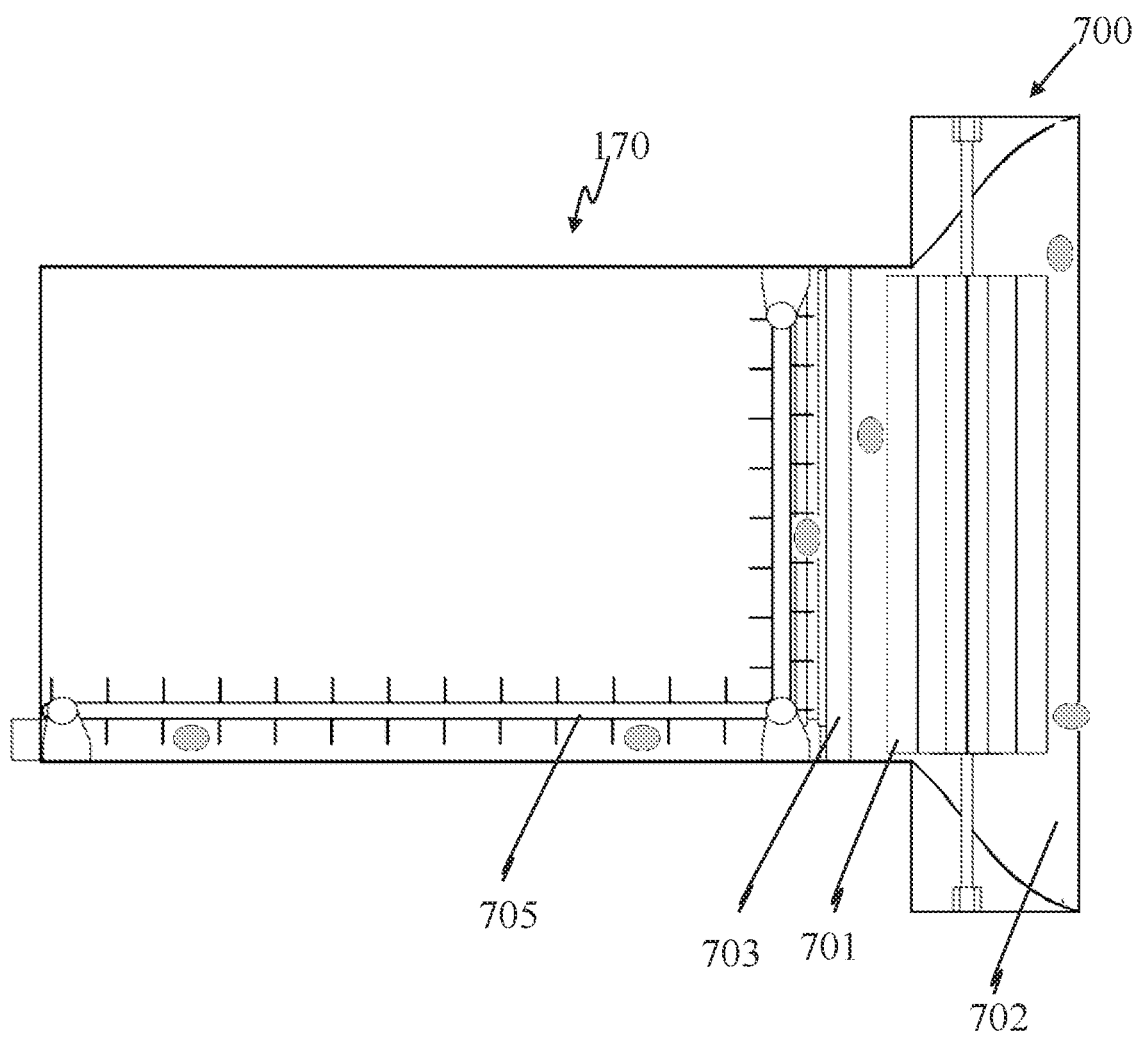
FIG. 7B illustrates a top view of the egg collection device for collecting floor eggs from a poultry farm, according to an embodiment of the present disclosure.

In an embodiment, the plurality of devices 170 as used herein relates to mechanical or electronic equipment that are mounted on the automated guided vehicle 110 to perform various operations such as processing litter, collecting litter, supplying water, removing deadstock, and collecting eggs. The plurality of devices 170 includes a handling device 200 (as shown in FIG. 2 in detail) for removal of dead or unhealthy livestock from the poultry farm, a humidity control device 300 (as shown in FIG. 3 in detail) for humidifying or dehumidifying air inside the poultry farm, a litter processing device 400 (as shown in FIG. 4 in detail) for processing litter inside the poultry farm, a litter collection device 500 (as shown in FIG. 5 in detail) for collecting litter inside the poultry farm, a line cleaner device 600 (as shown in FIG. 6 in detail) for cleaning the drinkers and feeders inside the poultry farm, and an egg collection device 700 (as shown in FIG. 7A and FIG. 7B in detail) for collecting eggs from the floor inside the poultry farm. The plurality of devices 170 are discussed in subsequent figures herein details.

According to an embodiment, the automated guided vehicle 110 includes the plurality of wheels 112 coupled to the body 111 and adapted to move the automated guided vehicle 110 inside the poultry farm. As used herein the plurality of wheels 112 is provided for movement of the automated guided vehicle 110 inside the poultry farm. In an example, the plurality of wheels 112 may include two wheels, three wheels, four wheels, five wheels, six wheels, and so forth. In an embodiment, referring to FIG. 1A, the plurality of wheels 112 includes four wheels located at four corners of the automated guided vehicle 110. In an embodiment, each of the plurality of wheels 112 is configured to rotate independently in synchronization with each other and with 180 degrees of rotation. In another embodiment, the u-shaped body 111 provided with slots 117 to enable a mounting of the plurality of devices 170 thereto and a plurality of wheel attachments 112.

Furthermore, the automated guided vehicle 110 is configured to assume an arbitrary position or free movement in any direction at any given point. In an example, the automated guided vehicle 110 is in front of an obstacle, then since the plurality of wheel attachments 112 are configured to rotate independently, the automated guided vehicle 110 may direct backward or diagonally, or according to the situation that allows a safe movement thereat. Owing to the independent driving of the wheels 112, the automated guided vehicle 110 moves inside the farm without getting stuck up irrespective floor conditions like deep litter, wet litter, soft litter or no litter.

According to another embodiment, the wheels are designed to work on AC or DC supply. The automated guided vehicle 110 is designed to move inside the farm in absence of overhead power railing 120 which supplied the power through a connector line 127. Within built or externally attached battery storage is used to power the wheels 112 and the plurality of sensors 113 to perform the required operation seamlessly According to another embodiment, the plurality of sensors 113 is adapted to capture environmental parameters at floor level inside the poultry farm. As used herein, the plurality of sensors 113 may include temperature sensors, proximity sensors, atmospheric sensors that provide data to the automated guided vehicle 110. Such data may include a location, temperature, humidity, air quality parameters, litter condition and the like. Furthermore, the plurality of sensors 113 is coupled at the slots 117 and/or on the body 111.

The automated guided vehicle 110 includes the collection bin 114 at a rear end 116 of the automated guided vehicle 110 to receive at least one of the litter, eggs, and wastewater. The collection bin 114 as used herein refers to a container the stores litter, eggs, and wastewater. Furthermore, the collection bin 114 may include anti corrosion materials such as steel and leakproof design. The automated guided vehicle 110 also includes the detachable protection arrangement 160 at a front 115 of the body 111. The detachable protection plate 161 as used herein refers to a protective shield coupled to the front 115 of the body 111 to protect the automated guided vehicle 110 from any damage due to obstacles or harm to livestock while moving inside the poultry farm.

Now referring to FIGS. 1A, 1B, and 1C, a vertical water supply line 140 with a pump 142 at a top end is configured to supply fresh water from a fresh water line 132 of the open overhead utility line 130 to the automated guided vehicle 110. The open overhead utility line 130 is fluidically coupled to the vertical water supply line 140 with the pump at the top end and operatively coupled to the automated guided vehicle 110. Referring to FIG. 1B and FIG. 1C, the overhead utility line 130 includes a hanger 131, the fresh water line 132, and a retriever channel 133. In an embodiment, the hanger 131 is adapted to couple the overhead utility line 130 to a surface, such as roof, of the poultry farm.

The vertical water supply line 140 with the pump 142 is provided to supply fresh water from the fresh water line 132 of the open overhead utility line 130 that opens to the collection bin 114 of the automated guided vehicle 110. As shown in FIG. 1D, the vertical conveyor arrangement 150 is adapted to retrieve the litter, eggs, or wastewater from the collection bin 114 and dispose in the retriever channel 133 of the open overhead utility line 130 via a disposal port 152. The vertical conveyor arrangement 150 conveys the litter, eggs, or wastewater collected from the poultry farm that is contained in the collection bin 114 and dispose the litter, eggs, or wastewater in the retriever channel 133 of the open overhead utility line 130.

In a scenario, when the automated guided vehicle 110 is configured to collect litter, then the vertical water supply line 140 supplies fresh water from the fresh water line 132 to the collection bin 114 and the vertical conveyor arrangement 150 draws the wastewater that is mixed with litter and opens out to the retriever channel 133. Furthermore, the retriever channel 133 is connected to a sewage treatment chamber to treat the litter and wastewater. In another scenario, when the automated guided vehicle 110 is configured to collect eggs, the vertical conveyor arrangement 150 draws from the collection bin 114 to the retriever channel 133 that opens to a repository that stores eggs.

The retriever channel 133 is fluidically coupled to the vertical conveyor arrangement 150, via the disposal port 152, to retrieve the litter or eggs from the collection bin 114. In the vertical conveyor arrangement 150, shelves and/or containers are coupled to an endless loop to form a conveyor 151 adapted to drain out the litter and wastewater that opens to the retriever channel 133. The shelves or container are rotatably coupled to the endless loop. Furthermore, the retriever channel 133 disposes the litter and/or the wastewater in the sewage treatment chamber to treat the litter and wastewater. Similarly, in case of egg collection the retriever channel 133 coupled to the collection bin 114 retrieves eggs from the containers coupled to an endless the vertical conveyor arrangement 150 to collect and store the eggs from the collection bin 114. In an embodiment, the retriever channel 133 also includes a conveyor belt system including an endless loop to transfer litter or wastewater or eggs from the collection bin 114 to an outer storage located at a distance from the livestock.

Now, referring to FIGS. 1E and 1F, the overhead power railing 120 is coupled to the body 111 of the automated guided vehicle 110 via the connector line 127. The overhead power railing 120 connects the automated guided vehicle 110 with an electrical power and data source lines through power stripes 123. The power stripes are further connected to a base station that provides instructions and power to the automated guided vehicle 110. Furthermore, the instructions may be programmed as a data to the automated guided vehicle 110 and/or a user can operate remotely on a real-time basis.

The overhead power railing 120 includes an assembly holder 121 coupled to a railing housing 122 positioned on a roof of the poultry farm. The assembly holder 121 as used herein refers to a mechanical coupling that may be a hanger that couples the railing housing 122 to the roof of the poultry farm. The overhead power railing 120 also includes a sliding contact head 124 coupled to the railing housing 122. The overhead power railing 120 is configured with the power strips 123 and adapted to transfer power or data to the automated guided vehicle 110 via the sliding contact head 124. In an embodiment, the data may be embodied as real-time data collected from the sensor 113. The data may be include information associated with at least one of environmental parameters, location, and operational parameters of the automated guided vehicle 110. In another embodiment, the data may be wirelessly communicated to a base station. In an embodiment, the sliding contact head 124 may be adapted to slide over the power strips 123 and simultaneously, enable power and data transmission through the power strip 123.

The sliding contact head 124 as used herein is the sliding mechanism that is adapted slide on the power stripes 123 of a stationary railing housing, i.e., the railing housing 122. The overhead power railing 120 also includes a wheel track 126 coupled to the railing housing 122 and adapted to ensure synchronized movement of the sliding contact head 124 with the automated guided vehicle 110. The overhead power railing 120 also includes a pair of motor-powered wheels 125 coupled to the sliding contact head 124 and configured to move on the wheel track 126. The overhead power railing 120 moves synchronously with the automated guided vehicle 110 using the sliding contact head 124, by moving the pair of motor-powered wheels 125 on the wheel track 126 which are coupled to the railing housing 122.

FIG. 2 illustrates the handling device 200 for the poultry farm, according to an embodiment of the present disclosure. It may be appreciated that the handling device 200 is one of the plurality of devices 170 that is mounted on the automated guided vehicle 110. The handling device 200 includes a robotic arm 201 with a gripper 202 arranged at the front end 205 along with an image processing-based control unit 203 to identify, lifting, and dropping of dead or unhealthy livestock in a collection bucket 204 at the rear end.

The handling device 200 as used herein refers to a pickup device mounted to the automated guided vehicle 110 to collect dead and/or unhealthy stocks from the poultry farm. The image processing-based control unit 203 is an image segregation device and/or a thermal imaging device that captures images of the live stocks and compares the captured images with a predetermined data from the overhead power railing 120 (as shown in FIGS. 1E and 1F) to locate a dead stock in between the live stocks. Additionally, the image processing-based control unit 203 is a standalone device that recognizes the dead stocks based on an orientation, color and/or activity of the live stocks and thereby actuates the robotic arm 201 to pick up the deadstock and drop inside the collection bucket 204.

FIG. 3 illustrates the humidity control device 300 for the poultry farm, according to an embodiment of the present disclosure. It may be appreciated that the humidity control device 300 is one of the plurality of devices 170 that is mounted on the automated guided vehicle 110. The humidity control device 300 includes a humidifying unit 301 to increase humidity of air inside the poultry farm using fresh water, and a dehumidifying unit 302 to lower the humidity of air inside the poultry farm by collecting and disposing the water using the vertical conveyor arrangement 150 and the overhead utility line 130.

Furthermore, the humidity control device 300 regulates the humidity of the poultry farm by increasing and decreasing the humidity as per requirement due to dropping and litter inside the poultry farm. The humidifying unit 301 may include evaporators, impeller humidifiers, steam vaporizers, and ultrasonic humidifiers that efficiently humidifies the surrounding near the live stocks in the poultry farm. Similarly, the dehumidifying unit 302 may include condensate dehumidifiers and desiccant dehumidifiers operable to dehumidify the surrounding near the live stocks in the poultry farm.

FIG. 4 illustrates the litter processing device 400 for processing a litter inside the poultry farm, according to an embodiment of the present disclosure. It may be appreciated that the litter processing device 400 is one of the plurality of devices 170 that is mounted on the automated guided vehicle 110. The litter processing device 400 includes a tiller head 401 positioned at a front end and operatively coupled to a power drive 402. The tiller head 401 is adapted to crush litter scattered on a floor of the poultry farm. The tiller head 401 is a crusher that includes blades to crumble the litter scattered on the floor of the poultry farm.

Furthermore, the power drive 402 is coupled to the tiller head 401 via power transmission mechanisms that drive the blades of the tiller head 401 to crush the litter inside the poultry farm. The litter processing device 400 also includes a heater unit 403 positioned at a rear side of the tiller head 401 and adapted to heat the crushed litter to lower the moisture content to a desired level of moisture. Further, the litter processing device 400 includes a disinfector spraying unit 405 positioned at a rear side of the heater unit 403 and configured to disinfect the crushed litter and remove bacteria, pathogens, microbes, and so forth.

The litter processing device 400 includes a disinfector storage tank 406 mounted on the disinfector spray unit 405 and adapted to pour disinfector on the crushed litter. In an embodiment, the litter processing device 400 also includes an ultraviolet light unit 404 disposed between the heater unit 403 and the disinfector spraying unit 405 and adapted to neutralize microbes inside the crushed litter. In an embodiment, the tiller head 401, the heater unit 403, the ultraviolet light unit 404, and the disinfector spraying unit 405, are sequentially arranged inside the litter processing device 400, and are interconnected to each other.

FIG. 5 illustrates a litter collection device 500 for collecting litter in the poultry farm, according to an embodiment of the present disclosure. It may be appreciated that the litter collection device 500 is one of the plurality of devices 170 that is mounted on the automated guided vehicle 110. Although, constructional and operational details of the litter collection device 500 are explained with respect to implementation in the poultry farm. However, it should be appreciated by a person skilled in the art that it should not be construed as limiting, and the litter collection device 500 can be equally implemented in animal husbandries or other livestock farms, without departing from the scope of the present disclosure.

The litter collection device 500 includes a rotary scooper 501 mounted proximate to a collector shovel 502 arranged at the front end with a level adjustment arrangement adapted to lift and gather litter.

Further, the level adjustment arrangement is operable to adjust a level of a belt conveyor 503 of the litter collection device 500, when the litter is loaded thereupon. The rotary scooper 501 is a rotatable scooper coupled with the collector shovel 502 that enables a scratching of a top layer of the litter that is chicken dropping or faeces from the floor of the poultry farm and thus collected by the rotary scooper 501. In absence of chicken's droppings or faeces, the ammonia formation lowers down, and avoids damaging floor material and/or replacement of bedding material. In order to remove complete litter, the collector shovel 502 is adjusted to the level of the poultry farm floor, so that complete litter gets collected.

The litter collection device 500 also includes the belt conveyor 503 positioned adjacent to the collector shovel 502 and operable to transfer the litter from the collector shovel 502 to the collection bin 114 mounted at a rear end of the belt conveyor 503. In an embodiment, as explained earlier, the collector bin 114 may be positioned at the rear end 116 of the automated guided vehicle 110 as shown in FIG. 1A.

A wiper plate 504 is positioned below the belt conveyor 503 to wipe out litter from the belt conveyor. A slope of the wiper plate 504 is towards collection bin 114. The entire arrangement of litter collection device 500 is enclosed using an enclosure 505. The enclosure 505 avoids splashing of litter outside the litter collection device 500, avoiding the contamination to feeder, drinker lines. Also, the enclosure 505 ensures the trapping of dust generated during scooping or collecting process, which avoids exposure of litter dust to livestock.

FIG. 6 illustrates a line cleaner device 600 for cleaning of feeder and drinker lines inside the poultry farm, according to an embodiment of the present disclosure. It may be appreciated that the line cleaner device 600 is one of the plurality of devices 170 that is mounted on the automated guided vehicle 110. The line cleaner device 600 includes an enclosed chamber 601 with collapsible doors 602 at the front and rear end to allow passage for a feeder 603 and a drinking water pan or line 604 adapted to avoid splashing of water outside the enclosed chamber 601. The line cleaner device 600 as used herein refers to a line cleaner equipment or machine that cleans the feeder and drinker line which are used to supply food stuff and water to live stock. The line cleaner device 600 is configured to provide water while cleaning the feeder 603 and the drinking water pan 604.

The line cleaner device 600 also includes a water sprayer 605 with a plurality of spray nozzles 606 for spraying water to clean the feeder 603 and the drinking water pan 604, a pair of a cleaner and dryer 607 to wipe out the water and dry out the feeder 603 and the drinking water pan 604, and a collecting pan 608 at the bottom to collect the wastewater after cleaning operation with a slope towards an outlet nozzle 609 connected to a collection chamber. The spray nozzles 606 sprays water on the litter either remove or prepare them soft that can be cleaned by the pair of a cleaner and dryer 607.

FIG. 7A illustrates a side view of an egg collection device 700 for collecting floor eggs from the poultry farm, according to an embodiment of the present disclosure. FIG. 7B illustrates a top view of the egg collection device 700 for collecting floor eggs from the poultry farm, according to an embodiment of the present disclosure. It may be appreciated that the egg collection device 700 is one of the plurality of devices 170 that is mounted on the automated guided vehicle 110. The egg collection device 700 includes a rotary sweeper 701 and a shovel 702 arranged at a front end of the egg collection device 700 and adapted to inwardly sweep eggs at a predefined speed. The rotary sweeper 701 refers to a collector provided with soft flaps that enable intake of the eggs at the predefined speed.

The egg collection device 700 also includes an egg collector plate 703 proximate to the rotary sweeper 701 and adapted to allow lifting of eggs swept from the rotary sweeper 701. The egg collector plate 703 is a panel below the rotary sweeper 701 to collect the eggs. The egg collection device 700 also includes a pair of rotatable bars 704 mounted parallel to each other at a distance to accommodate at least one egg thereupon and adapted to separate litter from eggs. The pair of rotatable 704 bars are arranged at a rear end of the egg collector plate 703 and configured to allow landing of eggs therein from the egg collector plate 703. Furthermore, the egg collection device 700 includes a horizontal conveyor 705 with spikes to guide or push the eggs on the rotatable bars 704 towards a collection bin 114.

While specific language has been used to describe the present disclosure, any limitations arising on account thereto, are not intended. As would be apparent to a person in the art, various working modifications may be made to the method in order to implement the inventive concept as taught herein. The drawings and the foregoing description give examples of embodiments. Those skilled in the art will appreciate that one or more of the described elements may well be combined into a single functional element. Alternatively, certain elements may be split into multiple functional elements. Elements from one embodiment may be added to another embodiment.

I claim:

1. A system for managing a poultry farm, the system comprising:
   an automated guided vehicle adapted to traverse inside the poultry farm, the automated guided vehicle comprising:

a body adapted to mount a plurality of devices configured to perform one or more operations inside the poultry farm;

a plurality of driving wheels coupled to the body and adapted to move the automated guided vehicle inside the poultry farm;

a plurality of sensors configured to sense environmental parameters at a floor level inside the poultry farm;

a collection bin at a rear end of the automated guided vehicle configured to receive at least one of litter, eggs, and wastewater; and a detachable protection arrangement at a front end of the automated guided vehicle;

an overhead power railing coupled to the automated guided vehicle via a connector line and configured to moves synchronously with the automated guided vehicle using a railing housing coupled to a sliding contact head and a plurality of motor-driven wheels configured to move on a wheel track;

an open overhead utility line fluidically coupled to a vertically disposed water supply line and a pump, the water supply line and the pump configured to supply fresh water from a fresh water line of the open overhead utility line to the collection bin of the automated guided vehicle; and a vertical conveyor arrangement adapted to retrieve the litter, eggs, and/or wastewater from the collection bin and dispose of the litter, eggs, and/or wastewater in a retriever channel of the open overhead utility line.

2. The system as claimed in claim 1, wherein the plurality of devices includes at least one of:
a handling device;
a humidity control device;
a litter processing device;
a litter collection device;
a line cleaner device;
an egg collection device.

3. The system as claimed in claim 1, wherein the automated guided vehicle includes a DC power input and an AC power input.

4. The system as claimed in claim 1, wherein each of the plurality of driving wheels is configured to rotate independently in synchronization with each of the other driving wheels and with 180 degrees of rotation.

5. The system as claimed in claim 1, wherein the body includes a u-shaped frame provided with a plurality of slots to enable a mounting of the plurality of devices thereto and a plurality of driving wheel attachments.

6. The system as claimed in claim 1, wherein the overhead power railing includes:
an assembly holder coupled to the railing housing; and
a plurality of power strips inside the railing housing, the sliding contact head adapted to slide over the plurality of power strips inside the railing housing.

7. The system as claimed in claim 2, wherein the handling device comprises:
a robotic arm with a gripper arranged at the front end of the automated guided vehicle along with an image processing-based control unit configured to identify lifting and dropping of dead or unhealthy livestock in a collection bucket.

8. The system as claimed in claim 2, wherein the humidity control device comprises:
a humidifying unit; and
a dehumidifying unit.

9. The system as claimed in claim 2, wherein the litter processing device comprises:
a tiller head operatively coupled to a power drive;
a heater unit;
a disinfector spraying unit; and
a disinfector storage tank mounted on the disinfector spraying unit.

10. The system as claimed in claim 9, wherein the litter processing device further comprises an ultraviolet light unit disposed between the heater unit and the disinfector spraying unit.

11. The system as claimed in claim 2, wherein the litter collection device comprises:
a rotary scooper mounted proximate to a collector shovel arranged at the front end of the automated guided vehicle;
a belt conveyor positioned between the collector shovel and the collection bin; and
an enclosure adapted to enclose the rotary scooper and the belt conveyor.

12. The system as claimed in claim 11, wherein the litter collection device further comprises a wiper plate positioned below the belt conveyor, the wiper plate having a slope that extends towards the collection bin.

13. The system as claimed in claim 2, wherein the line cleaner device comprises:
an enclosed chamber with collapsible doors to allow passage for a feeder (603) and a drinking water pan;
a water sprayer with a plurality of spray nozzles;
a pair of a cleaner and dryer; and
a collecting pan connected to an outlet nozzle adapted to convey wastewater to from the collecting pan to the collection bin.

14. The system as claimed in claim 2, wherein the egg collection device comprises:
a rotary sweeper and a shovel adapted to sweep eggs at a predefined speed;
an egg collector plate proximate to the rotary sweeper;
a pair of rotatable bars mounted parallel to each other at a distance that to accommodates a landing of at least one egg from the egg collector plate onto the pair of rotatable bars; and
a horizontal conveyor arrangement with spikes configured to guide or push eggs on the pair of rotatable bars towards the collection bin.

* * * * *